US00PP29424P3

(12) United States Plant Patent
Jackson et al.

(10) Patent No.: US PP29,424 P3
(45) Date of Patent: Jun. 26, 2018

(54) ***CORNUS* PLANT NAMED 'JN13'**

(50) Latin Name: *Cornus florida*
Varietal Denomination: JN13

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 50 days.

(21) Appl. No.: 15/530,037

(22) Filed: Nov. 22, 2016

(65) Prior Publication Data

US 2018/0146586 P1 May 24, 2018

(51) Int. Cl.
*A01H 5/02* (2018.01)
*A01H 5/04* (2018.01)

(52) U.S. Cl.
USPC ..... Plt./220
CPC ..... *A01H 5/02* (2013.01); *A01H 5/04* (2013.01)

(58) Field of Classification Search
USPC ..... Plt./220
See application file for complete search history.

*Primary Examiner* — Anne Marie Grunberg
(74) *Attorney, Agent, or Firm* — C. A. Whealy

(57) ABSTRACT

A new and distinct cultivar of *Cornus* plant named 'JN13', characterized by its upright and outwardly spreading plant habit; vigorous growth habit; developing leaves that are dark red in color becoming green with development; and single-type flowers that are red purple in color.

2 Drawing Sheets

Botanical classification: *Cornus florida*.
Cultivar designation: 'JN13'.

BACKGROUND OF THE INVENTION

The present invention relates to a new and distinct cultivar of *Cornus* plant, commercially grown as an ornamental deciduous tree, botanically known as *Cornus florida* and hereinafter referred to by the cultivar name 'JN13'.

The new *Cornus* plant is a product of a planned breeding program conducted by the Inventors in Belvidere, Tenn. The objective of the breeding program was to develop new *Cornus* plants with unique flower color.

The new *Cornus* plant originated from an open-pollination during the spring of 2010 in Belvidere, Tenn. of an unnamed selection of *Cornus Florida*, not patented, as the female, or seed, parent with an unknown selection of *Cornus florida* as the male, or pollen, parent. The new *Cornus* plant was discovered and selected by the Inventors as a single plant within the progeny of the stated open-pollination in a controlled nursery environment in Belvidere, Tenn. in the spring of 2011.

Asexual reproduction of the new *Cornus* plant by T-bud grafts in a controlled environment in Belvidere, Tenn. since the summer of 2011 has shown that the unique features of this new *Cornus* plant are stable and reproduced true to type in successive generations.

SUMMARY OF THE INVENTION

Plants of the new *Cornus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JN13'. These characteristics in combination distinguish 'JN13' as a new and distinct *Cornus* plant:

1. Upright and outwardly spreading plant habit.
2. Vigorous growth habit.
3. Developing leaves that are dark red in color becoming green with development.
4. Single-type flowers that are red purple in color.

Plants of the new *Cornus* differ primarily from plants of the female parent selection in the following characteristics:

1. Developing leaves of plants of the new *Cornus* are dark red in color whereas developing leaves of plants of the female parent selection are green in color.
2. Flowers of plants of the new *Cornus* are red purple in color whereas flowers of plants of the female parent selection are white in color.

Plants of the new *Cornus* can be compared to plants of *Cornus florida* 'Cherokee Brave', not patented. In side-by-side comparisons, plants of the new *Cornus* differ primarily from plants of 'Cherokee Brave' in the following characteristics:

1. Developing leaves of plants of the new *Cornus* are dark red in color whereas developing leaves of plants of 'Cherokee Brave' are green tinged with red.
2. Plants of the new *Cornus* and 'Cherokee Brave' differ in flower color as plants of 'Cherokee Brave' have medium red-colored flowers.

Plants of the new *Cornus* can be compared to plants of *Cornus florida* 'Cherokee Princess', not patented. In side-by-side comparisons, plants of the new *Cornus* differ primarily from plants of 'Cherokee Princess' in the following characteristics:

1. Developing leaves of plants of the new *Cornus* are dark red in color whereas developing leaves of plants of 'Cherokee Princess' are green in color.

2. In the autumn, leaves of plants of the new *Cornus* are dark red to orange in color whereas leaves of plants of 'Cherokee Princess' are medium orange to red in color.
3. Plants of the new *Cornus* and 'Cherokee Princess' differ in flower color as plants of 'Cherokee Princess' have white-colored flowers.

BRIEF DESCRIPTION OF THE PHOTOGRAPHS

The accompanying colored photographs illustrate the overall appearance of the new *Cornus* plant showing the colors as true as it is reasonably possible to obtain in colored reproductions of this type. Colors in the photographs may differ slightly from the color values cited in the detailed botanical description which accurately describe the colors of the new *Cornus* plant.

The photograph on the first sheet is a side perspective view of a typical plant of 'JN13' grown in an outdoor nursery during the summer.

The photograph on the second sheet is a close-up view of typical flowers 'JN13' and 'Cherokee Brave' (flowering stem in the foreground and being held) during the spring.

Plants used for in the photographs were grown in ground beds in an outdoor nursery in Winchester, Tenn. and under cultural practices typical of commercial *Cornus* production. Plants were two years old when the photographs were taken. During the production of the plants, day temperatures averaged 20.9° C. and night temperatures averaged 8.4° C.

DETAILED BOTANICAL DESCRIPTION

Plants used for the following observations, measurements and values were grown during the spring, summer and autumn in five-gallon containers in an outdoor nursery in Park Hill, Okla. and under cultural practices typical of commercial *Cornus* production. Plants were three years old when the description was taken. During the production of the plants, day temperatures averaged 21.9° C. and night temperatures averaged 15.5° C. In the following description, color references are made to The Royal Horticultural Society Colour Chart, 2007 Edition, except where general terms of ordinary dictionary significance are used.

Botanical classification: *Cornus florida* 'JN13'.

Parentage:

*Female, or seed, parent*.—Unnamed selection of *Cornus florida*, not patented.

*Male, or pollen, parent*.—Unknown selection of *Cornus florida*, not patented.

Propagation information:

*Type*.—By T-budding the new *Cornus* plant onto an unnamed selection of *Cornus florida* understock.

Plant description:

*Plant form and growth habit*.—Upright and outwardly spreading deciduous tree; vigorous growth habit; rapid growth rate.

*Plant height*.—About 97 cm.

*Plant width* (*spread*).—About 110 cm.

*Lateral branches*.—Aspect: Upright to sweeping outwardly. Length: About 75 cm. Diameter: About 1.2 cm. Internode length: About 9 cm. Strength: Strong, flexible. Texture and luster, developing branches: Smooth, glabrous; matte. Texture and luster, mature branches: Woody, slightly rough; matte. Color, developing branches: Close to 146A tinged with close to N187A. Color, mature branches: Slightly darker than N200B.

Leaf description:

*Arrangement*.—Opposite, simple.

*Length*.—About 13.75 cm.

*Width*.—About 8.25 cm.

*Shape*.—Ovate to elliptical.

*Apex*.—Acuminate with cuspidate tendencies.

*Base*.—Cuneate with obtuse tendencies.

*Margin*.—Entire; undulate.

*Texture and luster, upper and lower surfaces*.—Smooth, glabrous; matte.

*Venation pattern*.—Pinnate.

*Color, spring and summer*.—Developing leaves, upper surface: Close to N137A heavily overlain with close to 187B; venation, close to N137A tinged with close to N187B. Developing leaves, lower surface: Close to 146B; greyed color from upper surface shows through, close to 187B; venation, close to 146B. Fully expanded leaves, upper surface: Close to N137A; venation, close to N137A, proximally, midvein slightly tinged with close to N187B. Fully expanded leaves, lower surface: Close to 146B; venation, close to 146B.

*Color, autumn*.—Fully developed leaves, upper surface: Close to 200A with hints of close to 187A; venation, close to 200B to 200C. Fully developed leaves, lower surface: Close to 146B; color from upper surface shows through, close to 187B; venation, close to 146C to 146D.

*Petioles*.—Length: About 1.4 cm. Diameter: About 2 mm. Texture and luster, upper and lower surfaces: Smooth, glabrous; matte. Color, upper surface: Close to N137A tinged with close to N187A. Color, lower surface: Close to 146B.

Flower description:

*Flower appearance and arrangement*.—Single cruciform flower; flowers face mostly upright.

*Natural flowering season and flower longevity*.—Plants flower during the spring in Tennessee; flowers not persistent.

*Fragrance*.—None detected.

*Flower diameter*.—About 4 mm.

*Flower length*.—About 3 mm.

*Flower buds*.—Length: About 1.5 mm. Diameter: About 1 mm. Shape: Oval. Color: Close to 142B.

*Petals*.—Quantity and arrangement: Four in a single whorl. Length: About 1.5 mm. Width: About 1.5 mm. Shape: Cuneate. Apex: Acute. Base: Truncate. Margin: Entire. Texture and luster, upper and lower surfaces: Smooth, glabrous; glossy. Color: When opening, upper and lower surfaces: Close to 143C. Fully opened, upper and lower surfaces: Close to 142B.

*Sepals*.—Quantity and arrangement: Four in a single whorl. Length: About 1.5 mm. Diameter: About 2 mm. Shape: Cuneate. Apex: Acute. Base: Rounded. Margin: Entire. Texture and luster, upper and lower surfaces: Smooth, glabrous; matte. Color: When opening, upper and lower surfaces: Close to 139C. Fully opened, upper and lower surfaces: Close to 141B.

*Flower bracts*.—Quantity and arrangement: Four in a single whorl. Length: About 3.5 cm. Width: About 2.1 cm. Shape: Oval. Apex: Emarginate. Base: Obtuse. Margin: Entire. Texture and luster, upper and lower surfaces: Smooth, glabrous; glossy. Color:

When opening, upper and lower surfaces: Close to 59B. Fully opened, upper and lower surfaces: Close to 63A; towards the base and towards the apex, close to 62D.

*Peduncles*.—Length: About 0.5 mm. Diameter: About 0.5 mm. Aspect: Mostly erect. Strength: Strong, firm. Texture and luster: Smooth, glabrous; matte. Color: Close to 141C.

*Reproductive organs*.—Androecium: Quantity per flower: About four. Filament length: About 3 mm. Filament color: Close to 150B. Anther length: About 1.5 mm. Anther shape: Oval. Anther color: Close to 154C. Pollen amount: None observed. Gynoecium: Quantity per flower: One. Pistil length: About 4 mm. Style length: About 3 mm. Style color: Close to 150B. Stigma shape: Oval. Stigma color: Close to 150C.

*Fruits and seeds*.—Fruit and seed development have not been observed on plants of the new *Cornus* to date.

Pathogen & pest resistance: Plants of the new *Cornus* have not been observed to be resistant to pathogens and pests common to *Cornus* plants to date.

Garden performance: Plants of the new *Cornus* have been observed to have good garden performance and to be tolerant to high temperatures about 43° C. and low temperatures about −29° C.

It is claimed:

1. A new and distinct *Cornus* plant named 'JN13' as illustrated and described.

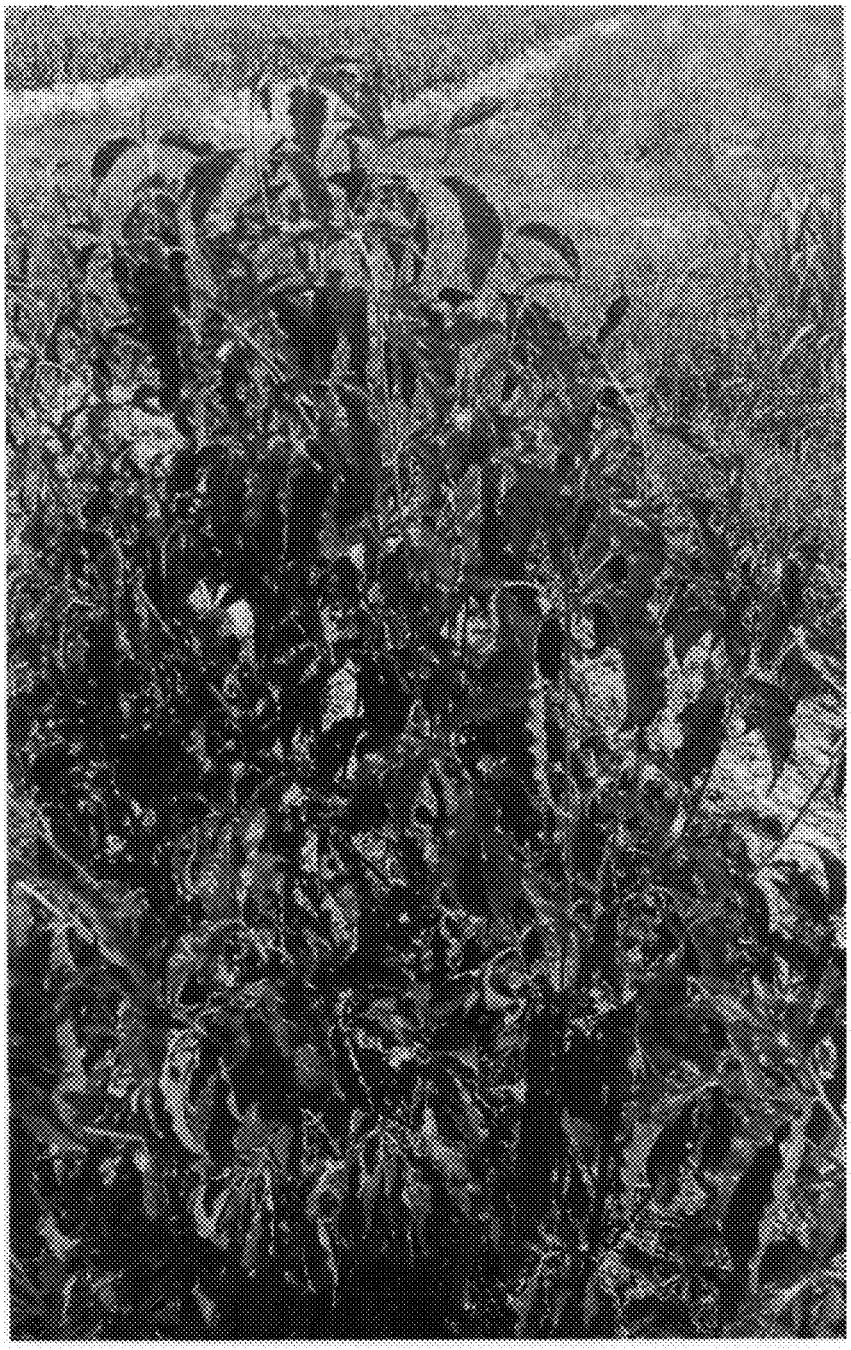

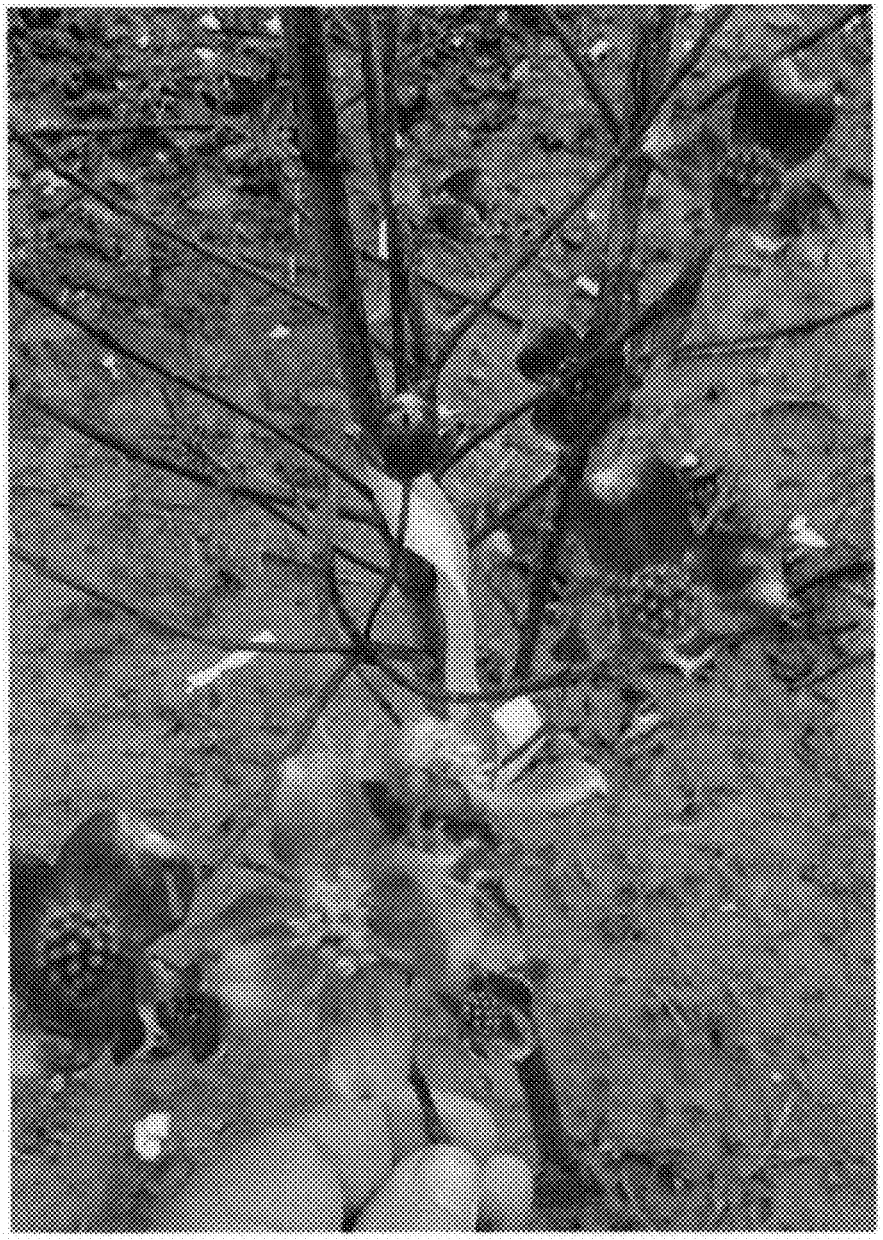

* * * * *